United States Patent [19]

Rydell

[11] Patent Number: 4,773,432

[45] Date of Patent: Sep. 27, 1988

[54] BAIL-OUT CATHETER

[75] Inventor: Mark A. Rydell, Golden Valley, Minn.

[73] Assignee: Schneider-Shiley (USA) Inc., Minneapolis, Minn.

[21] Appl. No.: 12,143

[22] Filed: Feb. 9, 1987

[51] Int. Cl.$^4$ ............................................. A61M 25/00
[52] U.S. Cl. .................................... 128/772; 604/264
[58] Field of Search .............................. 128/656–658, 128/772, 343, 344, 348.1; 604/264

[56] References Cited

U.S. PATENT DOCUMENTS

| | | | |
|---|---|---|---|
| 399,540 | 3/1889 | Lee | 604/264 |
| 1,667,443 | 4/1928 | Simonsen | 604/264 |
| 3,841,308 | 10/1974 | Tate | 128/772 |
| 4,080,706 | 3/1978 | Heilman et al. | 128/772 |
| 4,279,252 | 7/1981 | Martin | 128/658 |
| 4,577,637 | 3/1986 | Mueller | 128/658 |

Primary Examiner—Dalton L. Truluck
Attorney, Agent, or Firm—Orrin M. Haugen; Thomas J. Nikolai; Frederick W. Niebuhr

[57] ABSTRACT

A catheter for maintaining the patency of a blood vessel damaged during the course of angiography or angioplasty procedures comprising a toroidal coil whose adjacent turns are tightly wound and in contact with one another over a majority of the length thereof but which are separated from one another over a predetermined longitudinal dimension near the distal end thereof. The tightly wound touching coils may be covered with a Teflon coating and when the catheter must be used to maintain patency in a coronary artery, it is advanced along the guide wire of an angiography or angioplasty catheter until the open turn portion of the bail-out catheter bridges the site of the damaged vessel. After the angiographic or angioplasty catheter and its guide wire are removed, the bail-out catheter remains in position so that blood can flow through the open turns of that catheter and beyond until such time as surgical repair can be made.

1 Claim, 1 Drawing Sheet

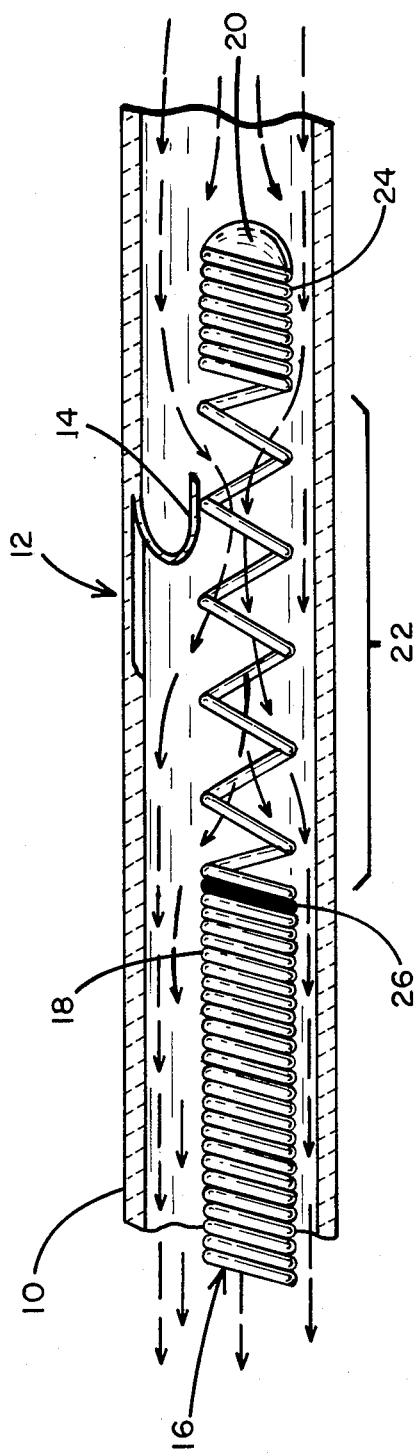

BAIL-OUT CATHETER

BACKGROUND OF THE INVENTION

I. Field of the Invention

This invention relates generally to medical apparatus used in a catheterization lab, and more particularly to a so-called "bail-out catheter" to be used in an emergency situation where the endothelial layer of a coronary blood vessel has been torn during the catheterization procedure and means must be provided for maintaining the blood vessel in a patent condition to prevent cell starvation distally of the injury site.

II. Background of the Invention

In angiography procedures where it is desired to visualize a portion of an organ such as the heart, a guide wire may first be introduced through a surgical opening in a vein or artery and then advanced through the vascular system to a desired location. Following that procedure, an angiographic catheter is advanced along the guide wire until its distal end is proximate a coronary ostium. Then the guidewire is withdrawn. Next, a radiopaque fluid is to be injected to render the site visible on a fluoroscopic screen.

In a somewhat similar fashion, when coronary transluminal angioplasty procedures are to be used to dilate a stenotic lesion, a balloon catheter is routed through the vascular system to the site of the lesion and then the balloon is inflated to spread or open the blood vessel at the site of the lesion.

In carrying out the above procedures, it can happen that the endothelial layer of the blood vessel in the coronary artery can be damaged to the point where the vessel collapses or such that a flap-like remnant can pull loose from the wall of the blood vessel and potentially occlude the blood vessel. Should such an episode occur, it is essential that patency be restored before downstream heart tissue is starved of its necessary oxygen. Advanced Catheter Systems, Inc. of Mountain View, Calif., offers a bail-out catheter in the form of an elongated plastic tube which is provided with a pattern of holes approximately 0.020 in diameter near the distal end thereof, the idea being that blood can flow through these apertures and beyond the site of the blood vessel damage. It has been found, however, that this commercially available bail-out catheter may become non-operational after relatively short periods of time due to clotting of the blood in the pattern of apertures.

It is the purpose of the present invention to provide an implement for maintaining vessel patency until surgical correction can be performed in the event that an angiography or angioplasty procedure has damaged a coronary blood vessel. The tool or utensil comprises an elongated wire helix having an outside diameter permitting it to be inserted through a guiding catheter, and an I.D. permitting it to be advanced over a guidewire. Over a majority of its length, the turns of the helix are tightly wound and abut one another, but at the distal end, the turns of the helix are open. Once the open turn portion of the implement are appropriately positioned so as to bridge the site of the damaged blood vessel, the guidewire can be removed while leaving the helical bail-out catheter of the present invention in place. Now, blood can readily flow over the surface of the bail-out catheter and when the open turns are reached, the blood may flow between those turns and through the center of the open helix past the point where the vessel may have collapsed against the bail-out catheter.

OBJECTS

It is accordingly a principal object of the present invention to provide a surgical utensil which may rapidly be routed to the site of blood vessel damage resulting from angioplasty or angiography procedures for maintaining patency of that blood vessel until such time as the patient can be moved to an operating room and surgical intervention can be accomplished.

Another object of the invention is to provide an elongated wire helix capable of being inserted through the lumen of a guiding catheter and over a guidewire prior to the withdrawal and removal of such guide catheter or guidewire, the helix having a series of open turns proximate its distal end for facilitating the flow of blood through and beyond a damaged blood vessel site.

These and other objects and advantages of the invention will become apparent to those skilled in the art from the following detailed description of a preferred embodiment, especially when considered in conjunction with the accompanying drawing.

DESCRIPTION OF THE DRAWING

The drawing is a cross-sectional view through a damaged blood vessel illustrating the present invention in place to maintain vessel patency.

DESCRIPTION OF THE PREFERRED EMBODIMENT

Referring to the drawing, there is identified by numeral 10 a blood vessel which had previously been subject to the passage of an angiographic or angioplasty catheter therealong and at a location identified by numeral 12, a portion of the endothelial layer has been torn creating a flap of tissue 14 projecting downward into the blood vessel 10 in a fashion that could occlude the flow of blood through that vessel. After the cardiologist determines that surgical intervention will be necessary to repair the damaged blood vessel, some means must be provided for insuring that the cells downstream from the damaged site do not become deprived of oxygen and nutrients while waiting for a surgical team to prepare themselves and the patient for the surgical correction. It has been found that if the angiographic or angioplasty catheter is left in place, its size will limit the amount of blood which can flow through the blood vessel when thus occupied. Thus, after withdrawing the angiography or angioplasty catheter and before withdrawing is associated guidewire from the blood vessel, the cardiologist will pass the bail-out catheter 16 of the present invention over the guidewire of the angiography or angioplasty catheter and, subsequently, will strip the angiographic or angioplasty guidewire out of the blood vessel leaving the bail-out catheter of the present invention in place.

With continued attention to the drawing and especially to the constructional features of the catheter 16, it is seen to comprise an elongated helix which is preferably formed from stainless steel or some other suitable material. While only the distal end portion of the bail-out catheter 16 is shown in the drawing, it is to be understood that the turns of the helix are in a touching relationship over a majority of the length of the entire catheter from its proximal end to a point identified by numeral 18 a short predetermined distance proximal of the distal end 20 of the catheter. Beginning at point 18, the turns of the helix are spread over a zone indicated by bracket 22 and the last few distal turns of the helix are again closely spaced as at 24 before terminating in a rounded tip 20.

To add to its lubricity, the surface of the helix proximal of location 18 is preferably coated with a Teflon spray which facilitates its passage through the surrounding catheter bodies during installation. Furthermore, it has been expedient to insert a single turn or ring 26 at the location 18 where the helix turns are stretched open. This ring is preferably made of gold or any other highly radiopaque material and functions as a location marker. By inserting this turn 26 between adjacent turns in the stainless steel helix, the marker band does not increase the cross-sectional dimension of the catheter.

As can be seen in the drawing, the flap of tissue 14 which might otherwise occlude the blood vessel 10 is supported by the open convolutions of the elongated helix comprising the bail-out catheter and, as is indicated by the flow arrows, blood is able to pass through the open convolutions of the helix and then along the outer surface of the tightly wound turns of the helix in the space between the outside diameter of the catheter body 16 and the inner walls of the blood vessel 10.

While the bail-out catheter 16 is shown as being comprised of helically wound round wire, it is also contemplated that it can be fabricated from a helically wound flat ribbon as well. The outside diameter of the coated helix may be in the range of from 0.053 inches to 0.079 inches, but limitation to the size range is not to be inferred. Thus, it can be seen that the present invention provides an instrument for use in catheterization procedures to maintain a blood vessel in an open or patent condition in the event that it is damaged during a prior procedure to the point where it would otherwise collapse and occlude the blood vessel. The bail-out catheter of the present invention can remain in place within the patient until he can be brought to surgery for repair of the damaged vessel.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can he accomplished without departing from the scope of the invention itself.

What is claimed is:

1. A method of restoring and maintaining a blood vessel in a patent condition following damage to the endothelial lining thereof during the course of a catheterization procedure until surgical intervention can be accomplished, comprising the steps of:
    (a) removing the angiography/angioplasty catheter from said blood vessel, leaving a guide wire in place;
    (b) fitting the open distal end of an elongated wire helix over said guide wire, said wire helix having closely spaced, touching turns over a majority of its length and an integrally formed segment of spaced-apart turns proximate a distal end thereof; and
    (c) advancing said elongated wire helix over said guide wire until said integrally formed segment of spaced-part turns is juxtaposed with the site of damage to said endothelial lining to support said lining and preventing same from occluding said blood vessel.

* * * * *